United States Patent [19]

Tsukada

[11] Patent Number: 5,219,334
[45] Date of Patent: Jun. 15, 1993

[54] INFUSER WITH BALLOON FOR CONTINUOUSLY INFUSING LIQUID DRUG

[75] Inventor: Osamu Tsukada, Nagano, Japan

[73] Assignee: Tsukada Medical Research Co., Ltd., Tokyo, Japan

[21] Appl. No.: 499,425

[22] PCT Filed: May 24, 1989

[86] PCT No.: PCT/JP89/00515
§ 371 Date: Jun. 19, 1990
§ 102(e) Date: Jun. 19, 1990

[87] PCT Pub. No.: WO90/14115
PCT Pub. Date: Nov. 29, 1990

[51] Int. Cl.$^5$ .............................. A61M 37/00
[52] U.S. Cl. .................... 604/132; 604/890.1; 128/DIG. 12
[58] Field of Search ........... 604/118, 132, 246, 247, 604/890.1, 891.1; 128/DIG. 12

[56] References Cited

U.S. PATENT DOCUMENTS

| | | | |
|---|---|---|---|
| 3,797,492 | 3/1974 | Place | 604/890.1 |
| 3,817,248 | 6/1974 | Buckles et al. | 128/DIG. 12 |
| 4,626,243 | 12/1986 | Singh et al. | 604/141 |
| 4,741,733 | 5/1988 | Winchell et al. | 128/DIG. 12 |
| 4,784,648 | 11/1988 | Singh et al. | 604/141 |
| 4,795,437 | 1/1989 | Schulte et al. | 604/247 |
| 4,867,741 | 9/1989 | Portnoy | 604/185 |
| 4,904,239 | 2/1990 | Winchell et al. | 128/DIG. 12 |
| 4,998,918 | 3/1991 | Mimura | 604/132 |

FOREIGN PATENT DOCUMENTS 0206195 12/1986 European Pat. Off. .
0295504 12/1988 European Pat. Off. .
0399117 11/1990 European Pat. Off. .

Primary Examiner—Gene Mancene
Assistant Examiner—Frank A. LaViola

[57] ABSTRACT

An infuser with a balloon for continuously infusing a drug in liquid form comprises a tubular main body (1) having in axial alignment, a first portion (12) at a first end of the tubular main body, a second portion (13) at a second end of the tubular main body opposite the first end, a control portion (3) intermediate the two ends, and a balloon coaxial with the first portion (12). The first portion (12) has a check valve (121) which allows the drug to be infused therefrom into the infuser which is at the first end of the tubular main body (1) and has a flow path (11) for the drug. The second portion (13) allows the drug to be injected therefrom at the second end of the tubular main body (1). The control portion (3) for controlling outflow of the drug is provided in such a manner as to be adjacent to the second portion (13) allowing the drug to be injected therefrom. A plurality of holes (111) are formed in the tubular main body in such a manner as to extend through a wall thereof. The balloon (2) made from an elastic material is provided so as to surround the holes (111) with the perimeter (21) thereof being airtightly secured to the outer periphery of the tubular main body (1). When in use, a predetermined volume of the drug is infused into the balloon, and the drug is caused to be outwardly injected from the infuser over a long period of time via the control portion.

10 Claims, 4 Drawing Sheets

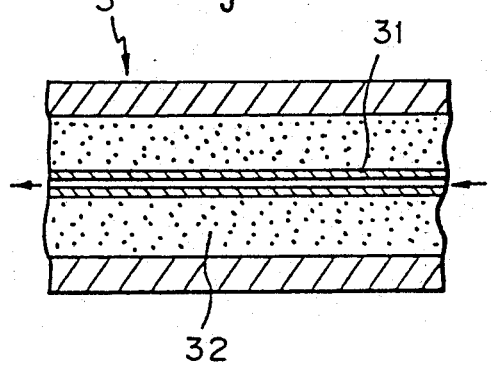
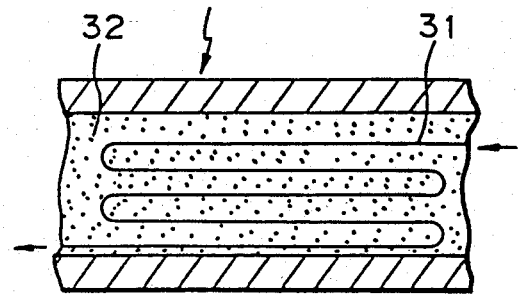
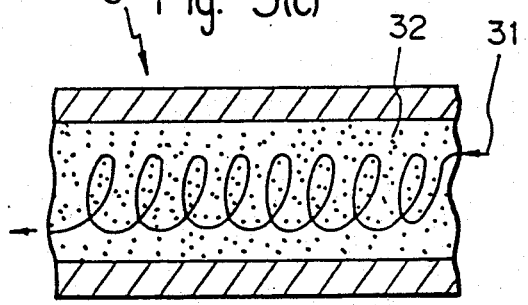
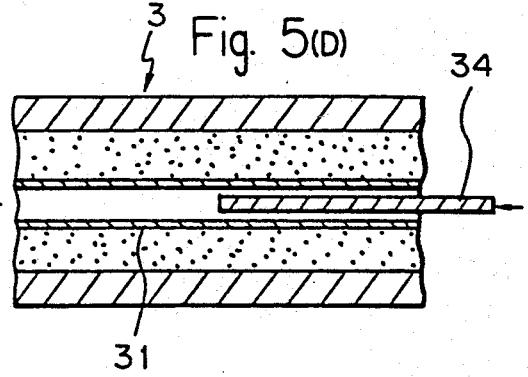
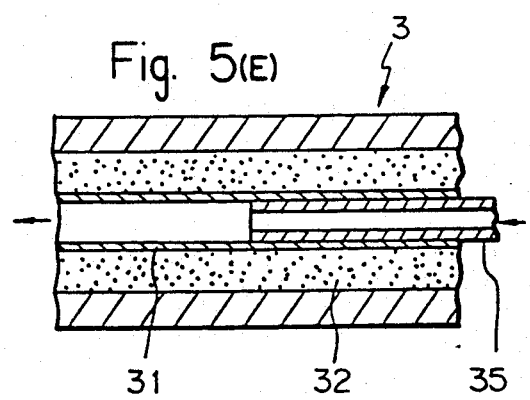
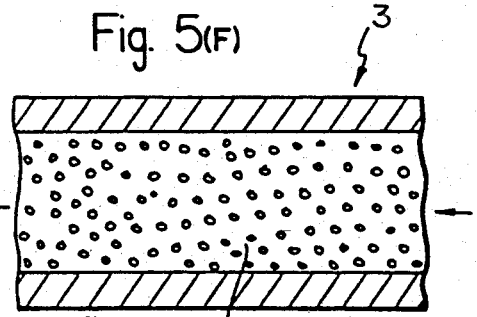

INFUSER WITH BALLOON FOR CONTINUOUSLY INFUSING LIQUID DRUG

TECHNICAL FIELD

The present invention relates to an infuser with a balloon for continuously infusing a drug in liquid form which is intended to be used in infusing into the human body a predetermined volume of a drug in liquid form that has already been infused into the balloon within a predetermined period of time.

BACKGROUND OF THE TECHNOLOGY

There are two conventional methods of infusing a drug in liquid form into the human body over a comparatively long period of time: in one method, a drug in liquid form is injected from an injecting needle or catheter which is attached to a syringe containing the drug in liquid form by operating the syringe manually, electrically or by utilizing the action of a spring; and in the other method, an instillation bottle containing a drug in liquid form is used, and the drug is caused to drip therefrom under gravity or in an electrical manner.

In a case where a drug in liquid form is infused into the human body over from a few minutes to a few hours, an injecting needle of a catheter must be kept attached to a syringe or instillation bottle serving as a drug supplier, and this causes great inconvenience to the operator as well as to the patient.

For instance, in a case where an infusion is continuously carried out in a manual fashion, the movement of both the patient and the operator is restricted for a certain period of time, and this gives them great pains mentally and physically. It is generally believed that people can take the same posture only for 1 or 2 minutes under such a condition. In contrast, in a case where the infusion of a drug is carried out electrically or by utilizing the action of a spring, a power source must be secured near the infusion site, and a syringe must properly be placed. This also restricts the action of the patient.

In addition, when a drug in liquid form is continuously infused into the human body by utilizing the instillation method, a comparatively large amount of a supplemental liquid relative to the drug needs to be used together, and even if the patient does not require such a supplemental liquid, he/she must be subject to the infusion of the same. Moreover, an instillation bottle or container must be placed at a position higher than where the patient is lying, and a complicated and long conduit is required to connect the injecting needle or catheter to the instillation bottle. This also restricts the movement of the patient, and the operator is required to confirm whether or not the instillation of a drug in liquid form is being carried out properly.

Japanese Patent Publication No. 45799/1980 discloses a flow control device for use in infusing a drug in liquid form into the human body. In this device, a core having a spiral groove formed therein is inserted in a sleeve, and this sleeve is clamped by means of a ring so as to control the flow of the liquid. However, with this flow control device, it is not possible to continuously infuse a drug in liquid form over a long period of time.

U.S. Pat. No. 4,318,400 discloses an infuser for continuously infusing a drug in liquid form. In this infuser, a balloon containing therein a drug in liquid form is inserted in a cylinder, and the balloon contracts in the axial direction with the drug in liquid form contained therein being injected therefrom by virtue of the contracting action of the balloon. However, this infuser is disadvantageous in that the liquid contained in the balloon cannot completely be discharged therefrom.

In view of the above drawbacks, the applicant of the present invention previously disclosed "An Infuser with a Balloon for Continuously Infusing a Drug in Liquid Form" (Japanese Patent No. 1384289) with a view to providing an infuser for continuously infusing a drug in liquid form that is intended to be used for continuously infusing a drug in liquid form into the human body over a comparatively long period of time and which is simple in construction, easy to handle and reliable in safety.

This patented infuser comprises a tubular main body having a flow path for a drug in liquid form that is formed along the longitudinal axis of the tubular main body, a portion with a check valve provided at one end of the tubular main body to allow a drug in liquid form to be infused therefrom into the tubular main body, a portion provided at the other end of the tubular main body to allow a drug in liquid form to be injected therefrom, a member provided at an intermediate position along the length of the tubular main body to shut off the flow path, an inlet hole and an outlet hole or outlet hole with a fine porous membrane provided in the neighborhood of the shutoff member on the drug infused portion side and drug injecting portion side, respectively, in such a manner as to extend through the wall of the tubular main body, and a balloon made from an elastic material and surrounding the inlet and outlet holes, the balloon being airtightly secured to the outer periphery of the tubular main body at the perimeter thereof.

In addition, the applicant of the present invention also previously disclosed "An Infuser with a Balloon for Continuously Infusing a Drug in Liquid Form into a Blood Vessel" (the Official, Gazette of Japanese Patent Public Disclosure No. 11465/1987) which comprises the above patented infuser and an intravascular retainer connected to the drug injecting portion of the same infuser.

Moreover, the applicant of the present invention also previously disclosed "An Infusing Catheter for Continuously Infusing a Drug in Liquid Form into a Urinary Bladder" (the Official Gazette of Japanese Patent Public Disclosure No. 11464/1987) that is intended to be used when continuously infusing a drug in liquid form into the human body over a comparatively long period of time and which is simple in construction, easy to handle and reliable in safety.

In this catheter, a conventional common catheter for a urinary bladder is employed, and a recess is formed in a part of the outer periphery of the catheter at the proximate end thereof. A balloon made from an elastic material is provided on the catheter so as to surround the recess, and the balloon is airtightly secured to the outer periphery of the catheter at the perimeter thereof. A capillary tube is provided on the wall of the catheter along the longitudinal axis thereof. This capillary tube is made open at the proximate end thereof so as to form an outlet port for a drug in liquid form and is caused to communicate with the recess at the proximate end. A portion allowing a drug in liquid form to be infused therefrom into the balloon is airtightly secured to the balloon at the central portion thereof, and a central passageway is provided at the center of the portion allowing the drug to be infused. A valve is provided on the central passageway a the inlet end thereof, and the passageway is caused to communicate with the recess at the outlet end thereof.

The above-described infuser or catheter is provided with a capillary hole or capillary tube for controlling the time during which a drug in liquid form is allowed to flow out. It is, however, difficult to actually form such a capillary hole or capillary tube, and even if this is possible, they are easy to be clogged with foreign matters.

In view of the above drawbacks, the applicant of the present invention succeeded in contriving a method of forming a capillary tube for controlling the time during which a drug in liquid form is allowed to flow out with ease and previously disclosed "An Infuser with a Balloon for Continuously Infusing a Drug in Liquid Form" having a structure in which the clogging of a capillary tube is prevented (PCT-JP-88-01055).

This infuser comprises a tubular main body having a flow path for a drug in liquid form that is formed along the longitudinal axis of the tubular main body. This tubular main body is provided with at one end thereof a portion with a check valve allowing a drug in liquid form to be infused therefrom into the tubular main body and a portion allowing a drug in liquid form to be injected therefrom at the other end thereof. A predetermined volume of a normal temperature or thermosetting pourable resin that exhibits no adhesiveness relative to a specific material is filled in the other end of the tubular main body, and a linear, spiral or winding capillary wire made from a specific material and having a predtermined diamter is embedded in the pourable resin. This capillary wire is caused to extend into the tubular main body at one end thereof, and at the other end thereof it is guided so as to extend through the drug injecting portion to the outside of the tubular main body. Holes are formed in the tubular main body in such a manner as to extend through the wall thereof, and a balloon made from an elastic material is provided so as to surround the holes with the perimeter thereof being airtightly fixed to the outer periphery of the tubular main body.

The capillary wire is drawn to the outside of the tubular main body so as to form a capillary hole through the pourable resin portion, and a retainer adapted to indwell the human body can be fitted to the drug injecting portion.

This drug infuser, however, has a drawback that minute burrs are caused on the inner surface of the capillary hole after the capillary wire has been drawn out. Thus, it is difficult to form a hole steadily functioning.

DISCLOSURE OF THE INVENTION

An object of the present invention is to provide a infuser with a balloon for continuously infusing a drug in liquid form in which the time during which a drug in liquid form is allowed to flow out is able to be variously changed and which has a steady capillary hole through which a drug in liquid form is allowed to flow out.

An infuser according to the present invention comprises a tubular main body having a flow path for a drug in liquid form that is formed along the longitudinal axis of the tubular main body. This tubular main body is provided with at one end thereof a portion with a check valve or one-way cock allowing a drug in liquid form to be infused therefrom into the tubular main body (hereinafter referred to as drug infused portion) and a portion allowing a drug in liquid form to be injected therefrom (hereinafter referred to as drug injecting portion) at the other end thereof. A control portion for controlling the outflow of a drug in liquid form is also provided adjacent to the drug infused portion at the other end of the tubular main body. A plurality of holes are formed in the tubular main body in such a manner as to extend through the wall thereof, and a balloon made from an elastic material is provided so as to surround the holes with the perimeter thereof being airtightly fixed to the outer periphery of the tubular main body.

In the control portion for controlling the drug's outflow, a capillary tube having a capillary hole and made from resin, metal, ceramic or the like is embedded in a synthetic resin. The portion may, instead, be filled with a porous or permeable and diffusible material.

The capillary tube is desirably embedded in the synthetic resin in a linear, winding or spiral fashion.

Alternatively, a capillary tube having a thin wire adapted to freely go in and out of a capillary hole formed therein and made from resin, metal, ceramic or the like is embedded in a synthetic resin in the above drug's outflow control portion. Instead, the capillary tube having a capillary hole and made from resin, metal, ceramic or the like may be inserted into a tube having a small diameter upon an intermediate position along the length of the tube, and both tubes are embedded in the synthetic resin.

BRIEF DESCRIPTION OF THE DRAWINGS

FIG. 5 shows longitudinal cross-sectional views, partially enlarged, of various modifications that can be made to the control portion of the infuser for continuously infusing a drug in liquid form according to the present invention that is adapted to control outflow of a drug in liquid form.

OPTIMAL EMBODIMENT OF THE INVENTION

Figure 1:
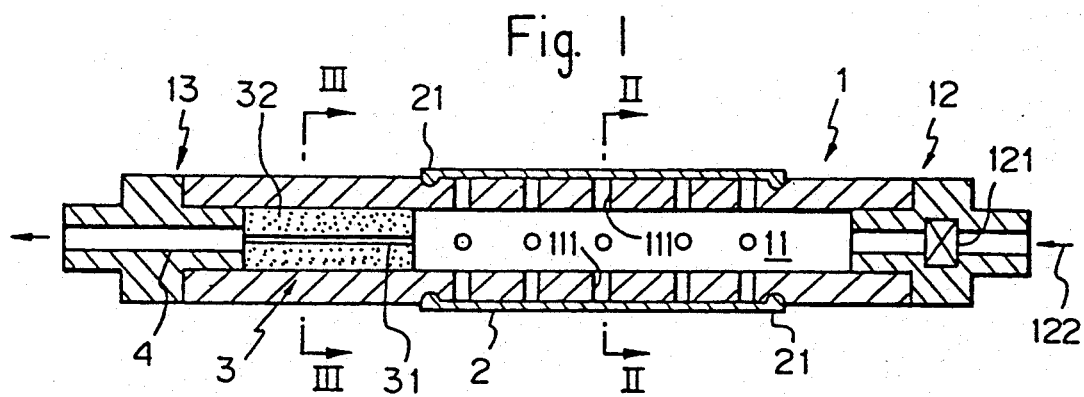
FIG. 1 is a longitudinal cross-sectional view of an infuser for continuously infusing a drug in liquid form according to the present invention.
Figure 2:
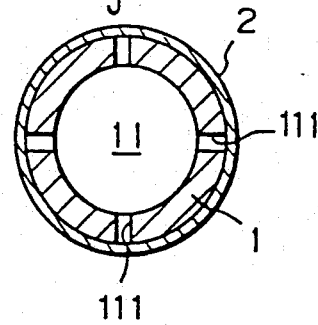
FIG. 2 is a transverse cross-sectional view taken along the line II—II of FIG. 1.
Figure 3:
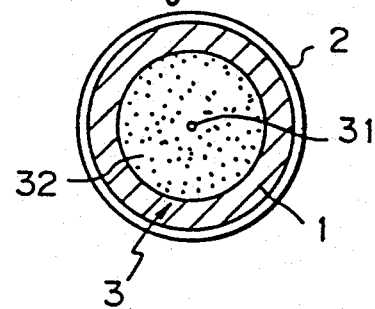
FIG. 3 is a transverse cross-sectional view taken along the line III—III of FIG. 1.

Referring to FIGS. 1 to 3, a basic structure of the infuser for continuously infusing a drug in liquid form according to the present invention will now be described. The drug infuser according to the present invention comprises a tubular main body 1 and a balloon 2.

In this tubular main body 1, a flow path 11 for a drug in liquid form is formed in such a manner as to extend in the longitudinal direction of the tubular main body. A portion 12 allowing a drug in liquid form to be infused therefrom into the tubular main body (hereinafter referred to as drug infused portion) is provided at one end (at the right-hand end as viewed in FIG. 1) of the tubular main body, while at the other end (at the left-hand end as viewed in FIG. 1) a portion 13 allowing a drug in liquid form to be injected therefrom (hereinafter referred to as drug injecting portion). These portions may be formed as an integral part of the tubular main body, but for reasons of convenience in the manufacturing and handling of infusers it is desirable to attach the relevant portions to the tubular main body 1 as separate parts as shown in FIG. 1. A conventional check valve or one-way cock 121 is provided in the drug infused portion 12. This check valve or one-way cock 121 may function such that it allows a drug in liquid form to be infused in the direction shown by a reference arrow 122, not allowing the drug to flow in the direction reverse to the one shown by the reference allow 122, or such that it opens and/or closes the passageway of a drug in liquid form.

A plurality of holes 111 are formed in the intermediate portion of the tubular main body 1 in such a manner as to extend through the wall thereof so as to communicate with the flow path 11 for a drug in liquid form. The balloon 2 surrounds the holes 111 and is airtightly secured to the outer periphery of the tubular main body 1 at the perimeter thereof. It is desirable that this balloon 2 is made from a material having good contraction and expansion properties, as well as good resistance to wear and toughness so that it is not easily damaged when a force is applied thereto from the outside. In particular, such a material is desirably transparent or translucent. Retailed silicon rubber, latex rubber and so forth can be used as an optimal material for such use.

Figure 6:
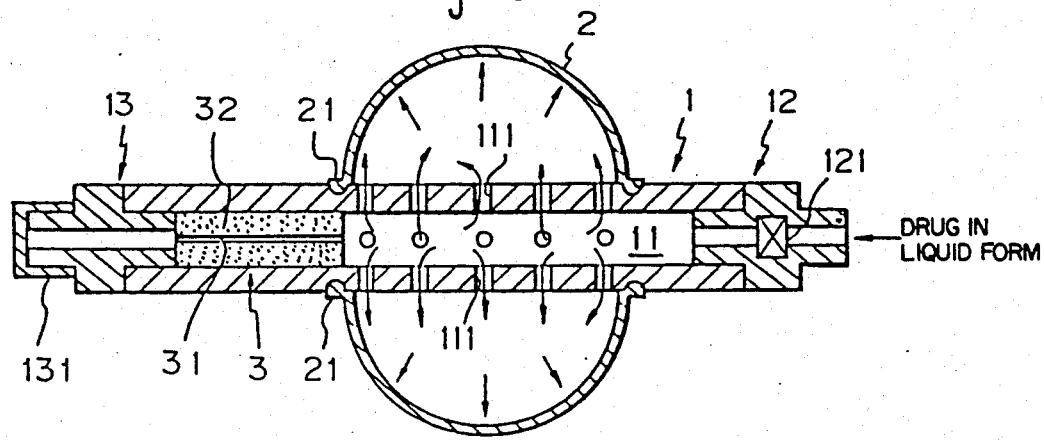
FIGS. 6 and 7 are explanatory views explaining the operation of the infuser for continuously infusing a drug in liquid form according to the present invention.

As shown in FIG. 1, the balloon 2 is tightly in contact with the tubular main body 1 over the whole portion thereof in a normal state in which the infusion of a drug in liquid form has not yet been started, while, as shown in FIG. 6, when it is put into operation with a drug in liquid form being started to be infused into the tubular main body 1, the balloon starts to separate from the outer periphery of the tubular main body 1 and expands with the perimeter 21 thereof being left secured to the tubular main body 1.

A control portion 3 for controlling outflow of a drug in liquid form is provided in the flow path 11 at a position that is more interior than the drug injecting portion 13. Various modifications of this outflow control portion 3 are shown in FIG. 5. FIGS. 5(A) to (E) show modification examples of the outflow control portion 3 wherein a capillary tube 31 having a capillary hole and made from resin, metal, ceramic or the like is embedded in a synthetic resin 32. The tube 31 may be embedded in the synthetic resin 32 in a linear (A), winding (B) or spiral (C) fashion. A hole may be formed through the synthetic resin 32 portion by means of laser or the like in order to replace the linear capillary tube 31.

FIG. 5(D) shows an example wherein a capillary wire 34 is inserted into the capillary tube 31 in such a manner as to be allowed to freely to in and out thereof, and FIG. 5(E) shows an example wherein a tube 35 having a diameter smaller than that of the tube 31 is inserted into the latter.

FIG. 5(F) shows an example wherein a porous material 33 is filled in the outflow control portion 3. Active carbon, pumice stone, resin particles, silicone gel, urethane gel and so forth may be used as a porous or permeable and diffusible material.

The length of the capillary hole of the tube 31 or porosity of the porous or permeable and diffusible material 33 can be one of the important factors to decide on the time during which a drug in liquid form is allowed to flow out.

Figure 7:
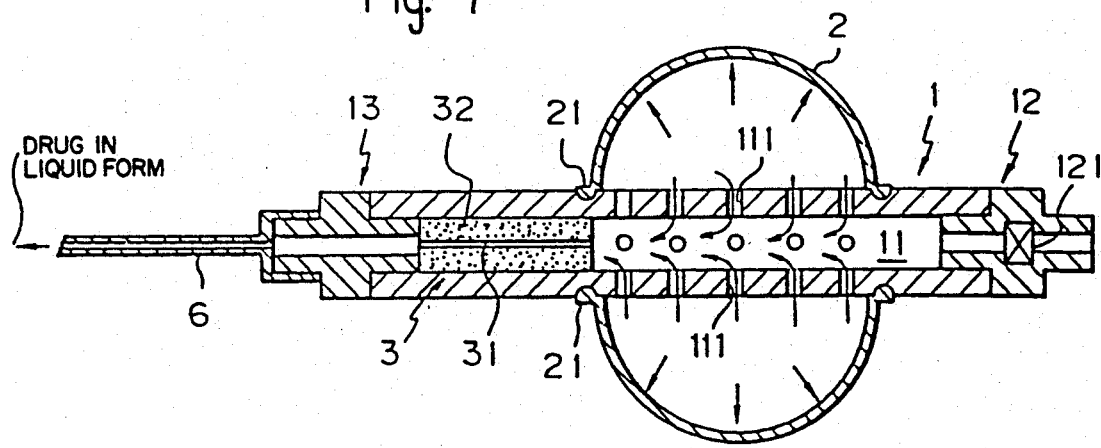

Referring to FIGS. 6 and 7, a functional example of the infuser for continuously infusing a drug in liquid form according to the present invention will now be described.

A predetermined volume of a drug in liquid form is infused into the infuser from the drug infused portion 12 of the infuser. The drug is caused to flow into the balloon 2 via the flow path 11 and holes 111 both formed in the tubular main body 1, thereby causing the balloon 2 to expand. The drug continues to be infused until the balloon becomes full thereof. The drug so infused into the balloon 2 is prevented from flowing in the reverse direction by means of the check valve or one-way cock 121.

In a case where the ingress of air into the balloon 2 or the flow path 11 for a drug in liquid form needs to be prevented, a drug in liquid form of the same type or isotonic sodium chloride solution may be infused into the flow path 11 in advance. Alternatively, the infuser should be erected in such a manner that the drug infused portion 12 becomes the top thereof. This allows air in the balloon 2 to enter the drug flow path 11 via the holes 111, and air in the drug flow path 11 eventually gathers in the vicinity of the drug infused portion 12. Air so gathering in the neighborhood of the drug infused portion 12 can be easily discharged by means of an air bleeding capillary tube (not shown).

After a predetermined volume of the drug has been infused into the balloon 2, a cap 131 attached to the distal end of the drug injecting portion 13 is then taken off, and a separately prepared necessary retainer adapted to indwell the human body, such as an injecting needle 6, is fitted to the drug injecting portion portion 13 instead (FIG. 7).

The drug filling the balloon 2 is caused to flow into the injecting needle 6 via the holes 111, drug flow path 11, capillary tube 31 having a capillary hole, and drug injecting portion 13 is virtue of the contracting action of the balloon 2.

Finally, a normal air bleeding operation is carried out. In order to confirm whether or not air is completely bleeded, the respective constituent elements should desirably be transparent or translucent.

The injecting time of the drug in liquid form depends on the volume of the drug infused in the balloon 2 and the viscosity of the drug, the contraction properties of the balloon 2, the transverse cross-sectional area and length of the capillary hole, the internal pressure of a part of the human body where the drug is infused, and so forth. The actual injecting time of the infuser may be measured by employing a standard drug in liquid form, and this may be carried out on each infuser.

Figure 4A:
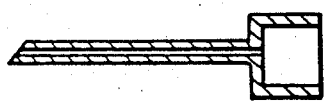
FIG. 4 shows side views of retainers adapted to indwell the human body and designed to be connected to the infuser for continuously infusing a drug in liquid form according to the present invention.
Figure 4B:
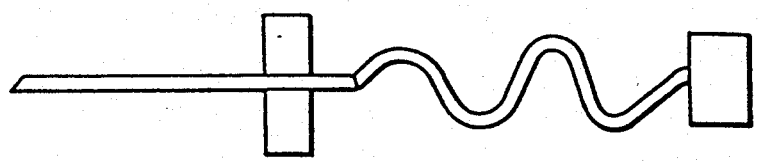
Figure 4C:
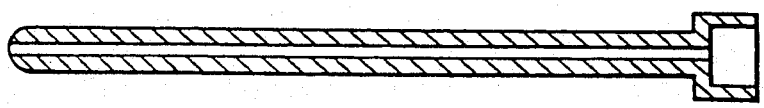

FIG. 4 shows main examples of retainers adapted to indwell the human body that may be connected to the drug injecting portion 13 of the infuser of the present invention. FIG. 4(A) shows a normal injecting needle, FIG. 4(B) an injecting needle having a flexible conduit, and FIG. 4(C) a normal catheter.

Basically, a spherical balloon 2 is employed in the present invention, but the balloon 2 used may be formed in any shapes depending on the infusing site of the human body. For instance, a flat elliptical balloon may be utilized.

Figure 8A:
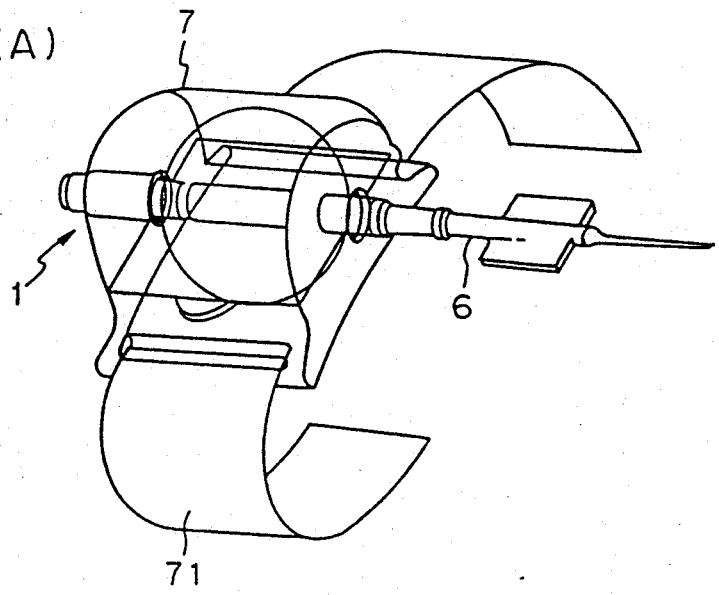
FIG. 8 is an explanatory view showing various applications of the infuser for continuously infusing a drug in liquid form according to the present invention.

A transparent cover 7 [FIG. 8(A)] covering the exterior of the balloon 2 may be detachably mounted on the tubular main body 1 for fear that the balloon is ruptured when it is brought into contact with an article having a sharp point, edge or the like. In this case, a belt 71 is preferably provided so as to facilitate the securing of the infuser to the human body.

Figure 8B:
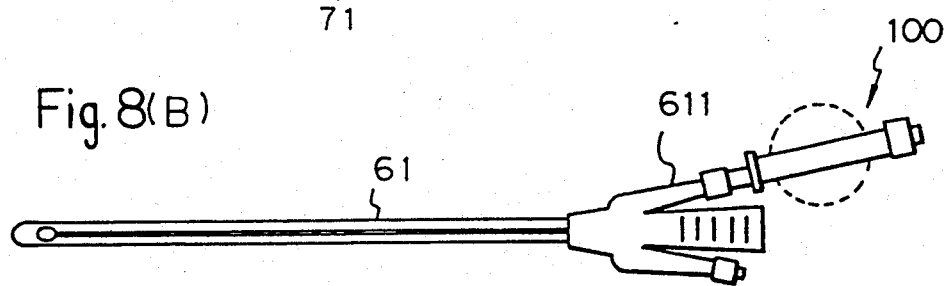

FIG. 8(B) shows an example wherein the infuser 100 for continuously infusing a drug in liquid form according to the present invention is connected to the drug infusing portion 611 of a catheter 61 for the urinary or digestive organs.

Figure 8C:
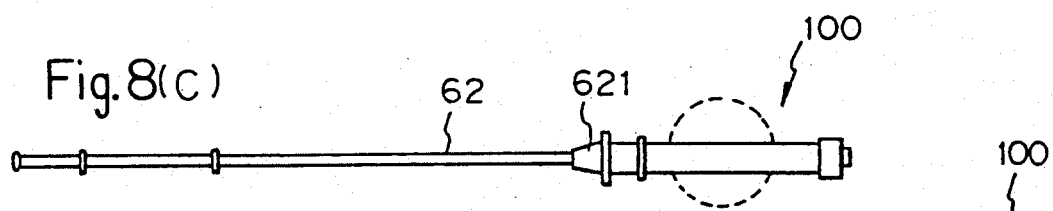

FIG. 8(C) shows an example wherein the infuser 100 for continuously infusing a drug in liquid form according to the present invention is connected to the drug infusing portion 621 of a catheter 62 for veins.

Figure 8D:
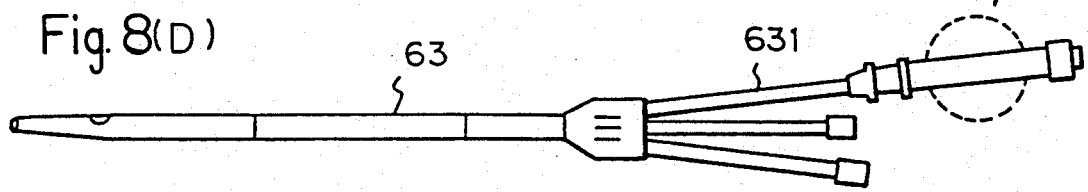

FIG. 8(D) shows an example wherein the infuser 100 for continuously infusing a drug in liquid form according to the present invention is connected to the drug infusing portion 631 of a catheter 63 for use in the field of obstetrics and gynecology.

Figure 8E:
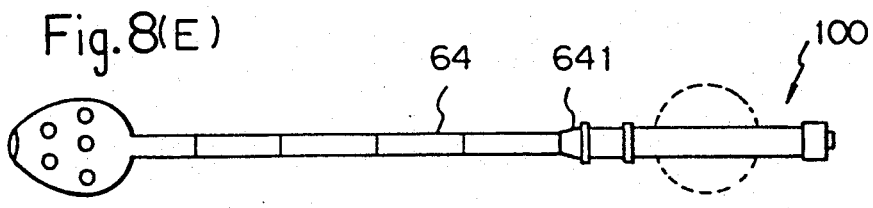

FIG. 8(E) shows an example wherein the infuser 100 for continuously infusing a drug in liquid form according to the present invention is connected to the drug infusing portion 641 of a catheter 64 for use in the field of encephalon surgery.

Since the infuser for continuously infusing a drug in liquid form in accordance with the present invention is adapted to function not only as a container for a drug but also as a drug infuser, it is simple in construction and easy to handle. Due to this the infuser of the present invention does not restrict the action and movement of the patient, and in addition it reduces the labour and actual working hours of the operator. Moreover, once air is bleeded, the ingress of air is not allowed until the balloon is completely contracted.

Furthermore, in the infuser in accordance with the present invention, since the formation of a capillary hole that greatly affects the infusing time is attained very easily and immediately before the infuser is used, there is no risk of the capillary hole being clogged.

POSSIBLE INDUSTRIAL APPLICATIONS

The infuser for continuously infusing a drug in liquid form in accordance with the present invention is able to be widely used as a medical appliance for human or animal.

I claim:

1. An infuser with a balloon for continuously infusing a drug in liquid form, comprising:
    an axially elongated tubular main body (1) having an inner peripheral surface and an outer peripheral surface defining a wall therebetween, an inner diameter and a flow path (11) defined by the inner diameter and formed along a longitudinal axis of said tubular main body (1) and through which a drug in liquid form flows;
    a plurality of holes (111) being formed in said tubular main body in such a manner as to extend through the wall thereof;
    a first portion (12) integral with a first end of said tubular main body (1) for receiving a drug in liquid form and having a check valve (121) integral with said first portion allowing the drug in liquid form to be infused therefrom into said tubular main body (1);
    a second portion (13) integral with a second end of said tubular main body (1) opposite said first end allowing the drug in liquid form to be injected therefrom;
    a control portion (3) for controlling outflow of the drug in liquid form and provided in the second end of said tubular main body (1) in such a manner as to be adjacent to and in communication with said second portion (13) allowing the drug in liquid form to be injected therefrom, and
    a balloon (2) in the shape of a sleeve made from an elastic material and disposed coaxially encircling said tubular main body (1) and surrounding said holes (111) with the perimeter (21) at each end of said balloon being airtightly secured to the outer periphery of said tubular main body (1), said balloon expanding to receive a drug in liquid form under pressure flowing from said main tubular body through said holes into the interior of said balloon thereby expanding said balloon and defining a container for holding and pressurizing the liquid drug and for forcing the liquid drug under pressure from the container through said plurality of holes (111) for ejection through said second portion.

2. An infuser with a balloon for continuously infusing a drug in liquid form, comprising:
    an axially elongated tubular main body (1) having an inner peripheral surface and an outer peripheral surface defining a wall therebetween, an inner diameter and a flow path (11) defined by the inner diameter and formed along a longitudinal axis of said tubular main body (1) and through which a drug in liquid form flows;
    a plurality of holes (111) being formed in said tubular main body in such a manner as to extend through a wall thereof;
    a first portion (12) integral with a first end of said tubular main body (1) for receiving a drug in liquid form and having a check valve (121) integral with said first portion allowing the drug in liquid form to be infused therefrom into said tubular main body (1);
    a second portion (13) integral with a second end of said tubular main body (1) opposite said first end allowing the drug in liquid form to be injected therefrom;
    a control portion (3) for controlling outflow of the drug in liquid form and provided in the second end of said tubular main body (1) in such a manner as to be adjacent to and in communication with said second portion (13) allowing the drug in liquid form to be injected therefrom, said control portion (3) further comprising a capillary tube (31) embedded in a synthetic resin (32) in a winding fashion, and
    a balloon (2) in the shape of a sleeve made from an elastic material and disposed coaxially encircling said tubular main body (1) and surrounding said holes (111) with the perimeter (21) at each end of said balloon being airtightly secured to the outer periphery of said tubular main body (1), said balloon expanding to receive a drug in liquid form under pressure flowing from said main tubular body through said holes into the interior of said balloon thereby expanding said balloon and defining a container for holding and pressurizing the liquid drug and for forcing the liquid drug under pressure from the container through said plurality of holes (111) for ejection through said second portion.

3. An infuser with a balloon for continuously infusing a drug in liquid form, comprising:

an axially elongated tubular main body (1) having an inner peripheral surface and an outer peripheral surface defining a wall therebetween, an inner diameter and a flow path (11) defined by the inner diameter and formed along a longitudinal axis of said tubular main body (1) and through which a drug in liquid form flows;

a plurality of holes (111) being formed in said tubular main body in such a manner as to extend through a wall thereof;

a first portion (12) integral with a first end of said tubular main body (1) for receiving a drug in liquid form and having a check valve (121) integral with said first portion allowing the drug in liquid form to be infused therefrom into said tubular main body (1);

a second portion (13) integral with a second end of said tubular main body (1) opposite said first end allowing the drug in liquid form to be injected therefrom;

a control portion (3) for controlling outflow of the drug in liquid form and provided in the second end of said tubular main body (1) in such a manner as to be adjacent to and in communication with said second portion (13) allowing the drug in liquid form to be injected therefrom, said control portion (3) further comprising a capillary tube (31) embedded in a synthetic resin (32) in a spiral fashion, and a balloon (2) in the shape of a sleeve made from an elastic material and disposed coaxially encircling said tubular main body (1) and surrounding said holes (111) with the perimeter (21) at each end of said balloon being airtightly secured to the outer periphery of said tubular main body (1), said balloon expanding to receive a drug in liquid form under pressure flowing from said main tubular body through said holes into the interior of said balloon thereby expanding said balloon and defining a container for holding and pressurizing the liquid drug and for forcing the liquid drug under pressure from the container through said plurality of holes (111) for ejection through said second portion.

4. An infuser as set forth in claim 1, wherein said control portion (3) allowing a drug in liquid form to be injected therefrom has a construction in which a capillary tube (31) having a capillary hole is embedded in a synthetic resin (32).

5. An infuser as set forth in claim 1, wherein said capillary tube (31) is embedded in said synthetic resin (32) in a linear fashion.

6. An infuser as set forth in claim 1, wherein said capillary tube (31) is embedded in said synthetic resin (32) in a winding fashion.

7. An infuser as set forth in claim 1, wherein said capillary tube (31) is embedded in said synthetic resin (32) in a spiral manner.

8. An infuser as set forth in claim 1, wherein said control portion (3) allowing a drug in liquid form to be injected therefrom is filled with a porous and diffusible material (33).

9. An infuser as set forth in claim 1, wherein said control portion (3) allowing a drug in liquid form to be injected therefrom has a construction in which a capillary wire (34) is inserted into said capillary tube (31) in such a manner as to freely go in and out thereof, and in which said capillary tube (31) and capillary wire (34) are embedded in said synthetic resin (32).

10. An infuser as set forth in claim 1, wherein said control portion (3) allowing a drug in liquid form to be injected therefrom has a construction in which said capillary tube (31) is inserted in a tube (35) having a small diameter up to an intermediate position along the length of said tube.

* * * * *